(12) United States Patent
Göhler et al.

(10) Patent No.: US 11,185,230 B2
(45) Date of Patent: Nov. 30, 2021

(54) TRANSMISSION APPARATUS FOR TRANSMITTING BRAIN PARAMETER SENSOR DATA

(71) Applicant: Raumedic AG, Münchberg (DE)

(72) Inventors: Karlheinz Göhler, Zwönitz (DE); Peter Peitsch, Erfurt (DE); Reinhard Jurisch, Meckfeld (DE)

(73) Assignee: Raumedic AG, Münchberg (DE)

( * ) Notice: Subject to any disclaimer, the term of this patent is extended or adjusted under 35 U.S.C. 154(b) by 1107 days.

(21) Appl. No.: 15/685,546

(22) Filed: Aug. 24, 2017

(65) Prior Publication Data
US 2018/0055362 A1    Mar. 1, 2018

(30) Foreign Application Priority Data
Aug. 24, 2016   (DE) .................... 20 2016 005 183.1

(51) Int. Cl.
*A61B 5/00* (2006.01)
*A61B 5/03* (2006.01)

(52) U.S. Cl.
CPC .......... *A61B 5/0031* (2013.01); *A61B 5/0006* (2013.01); *A61B 5/0026* (2013.01); *A61B 5/031* (2013.01); *A61B 5/4064* (2013.01); *A61B 5/6814* (2013.01); *A61B 2560/0204* (2013.01)

(58) Field of Classification Search
CPC ....... A61B 5/6803; A61B 5/01; A61B 5/0488; A61B 5/11; A61B 5/0024; A61B 5/04001; A61B 5/05; A61B 5/165; A61B 5/4094; A61B 5/6833; A61B 5/031; A61B 5/0402; A61B 5/0478; A61B 5/686; A61B 5/0031; A61B 5/0006; A61B 5/0026; A61B 5/4064; A61B 5/6814; A61B 2560/0204
USPC .................... 600/544, 546, 561; 607/15, 139
See application file for complete search history.

(56) References Cited

U.S. PATENT DOCUMENTS

| | | | | | |
|---|---|---|---|---|---|
| 4,967,038 | A | * | 10/1990 | Gevins ................. | A61B 5/6814 600/383 |
| 6,354,299 | B1 | * | 3/2002 | Fischell ............. | A61N 1/37217 128/899 |
| 8,337,413 | B2 | * | 12/2012 | Tauber ..................... | A61B 5/72 600/561 |
| 2008/0293446 | A1 | * | 11/2008 | Rofougaran ......... | H01Q 1/2283 455/552.1 |
| 2009/0112278 | A1 | * | 4/2009 | Wingeier ............. | A61B 5/4064 607/45 |

(Continued)

FOREIGN PATENT DOCUMENTS

| WO | 2009043431 | 4/2009 |
|---|---|---|
| WO | 2013017440 | 2/2013 |

*Primary Examiner* — May A Abouelela
(74) *Attorney, Agent, or Firm* — Boyle Fredrickson S.C.

(57) ABSTRACT

A transmission apparatus for the transmission of brain parameter sensor data includes,
  a receiving unit with an antenna, which can be wirelessly connected to a transmitting unit of a brain parameter sensor for data transmission,
  a data processing device which is in signaling connection to the receiving unit,
  a high frequency source for generating a data transmission carrier frequency,
  wherein the high frequency source is integrated in a housing of the data processing device.

The result is a transmission apparatus which is designed for use in a domestic patient environment.

15 Claims, 2 Drawing Sheets

(56) References Cited

U.S. PATENT DOCUMENTS

| | | | |
|---|---|---|---|
| 2009/0143696 A1* | 6/2009 | Najafi | A61B 5/076 600/561 |
| 2010/0041962 A1* | 2/2010 | Causevic | A61B 5/0478 600/301 |
| 2012/0165634 A1* | 6/2012 | Lee | A61B 5/00 600/345 |
| 2017/0043167 A1* | 2/2017 | Widge | A61B 5/0205 |

* cited by examiner

TRANSMISSION APPARATUS FOR TRANSMITTING BRAIN PARAMETER SENSOR DATA

CROSS-REFERENCE TO RELATED APPLICATIONS

The present patent application claims the priority of the German utility model application 20 2016 005 183.1, filed Aug. 24, 2016, pursuant to 35 U.S.C. 119(a)-(d), the content of which is incorporated herein by reference in its entirety as if fully set forth herein.

FIELD OF THE INVENTION

The invention relates to a transmission apparatus for transmitting brain parameter sensor data.

BACKGROUND OF THE INVENTION

Such transmission apparatuses are known from WO 2009/043 431 A1 and WO 2013/017 440 A1. US 2009/0143696 A1 describes a transmission apparatus for brain parameter data with an implant as well as an external receiving and data processing unit.

SUMMARY OF THE INVENTION

It is an object of the present invention to further develop a transmission apparatus of the initially mentioned type such that it is designed for use in a domestic patient environment.

In accordance with the invention, this object is achieved by a transmission apparatus for the transmission of brain parameter sensor data, with a receiving unit with an antenna, which can be wirelessly connected to a transmitting unit of a brain parameter sensor for data transmission, with a data processing device which is in signaling connection to the receiving unit, with a high frequency source for generating a data transmission carrier frequency, and wherein the high frequency source is integrated in a housing of the data processing device.

In accordance with the invention, it was recognized that it is not absolutely necessary to implement a high frequency source, which is necessary for the transmission of the brain parameter sensor data from a brain parameter sensor as a rule implanted to the receiving unit, as an externally shielded component with respect to the data processing device. Provided suitable precautions are taken for shielding, it is definitely possible to integrate the high frequency source in the housing of the data processing device without this leading to undesirable interference. The result is a very compact transmission apparatus which can be comfortably worn on the body, for example like a mobile phone.

A component arrangement, in which electronic components of the data processing device are arranged on a single printed circuit board in the housing, wherein the high frequency source is also arranged on the printed circuit board, further facilitates a compact structure of the data processing device. Expensive cabling can be omitted. Signal connections between the electronic components and/or components of the high frequency source can be configured as conducting paths on the printed circuit board.

A metallic shielding unit for shielding the high frequency source from the electronic components of the data processing device avoids undesirable interference through the high frequency source.

A housing design, in which the housing has a metallic front plate and a metallic base plate, both of which being borne by a circumferential housing frame made of plastic, is light and compact. The housing can consist of a total of exactly three components, namely the front plate, which can simultaneously be the printed circuit board, the base plate and the housing frame.

An interface for transmitting sensor data to an external device enables the transfer and external evaluation of the sensor data. A mobile memory can be coupled via the interface and/or the sensor data can be transmitted tethered or wirelessly over the interface. The interface can be a USB port. A WLAN interface is also possible.

The advantages of a sensor system with a transmission apparatus according to the invention and with a brain parameter sensor corresponding to those that have already been mentioned above with reference to the transmission report in accordance with the invention. The brain parameter sensor can be configured, such as, for example, described in WO 2009/043 431 A1 and WO 2013/017 440 A1.

BRIEF DESCRIPTION OF THE DRAWINGS

An exemplary embodiment of the invention is described in the following on the basis of the drawing.

DESCRIPTION OF AT LEAST ONE PREFERRED EMBODIMENT

Figure 1:
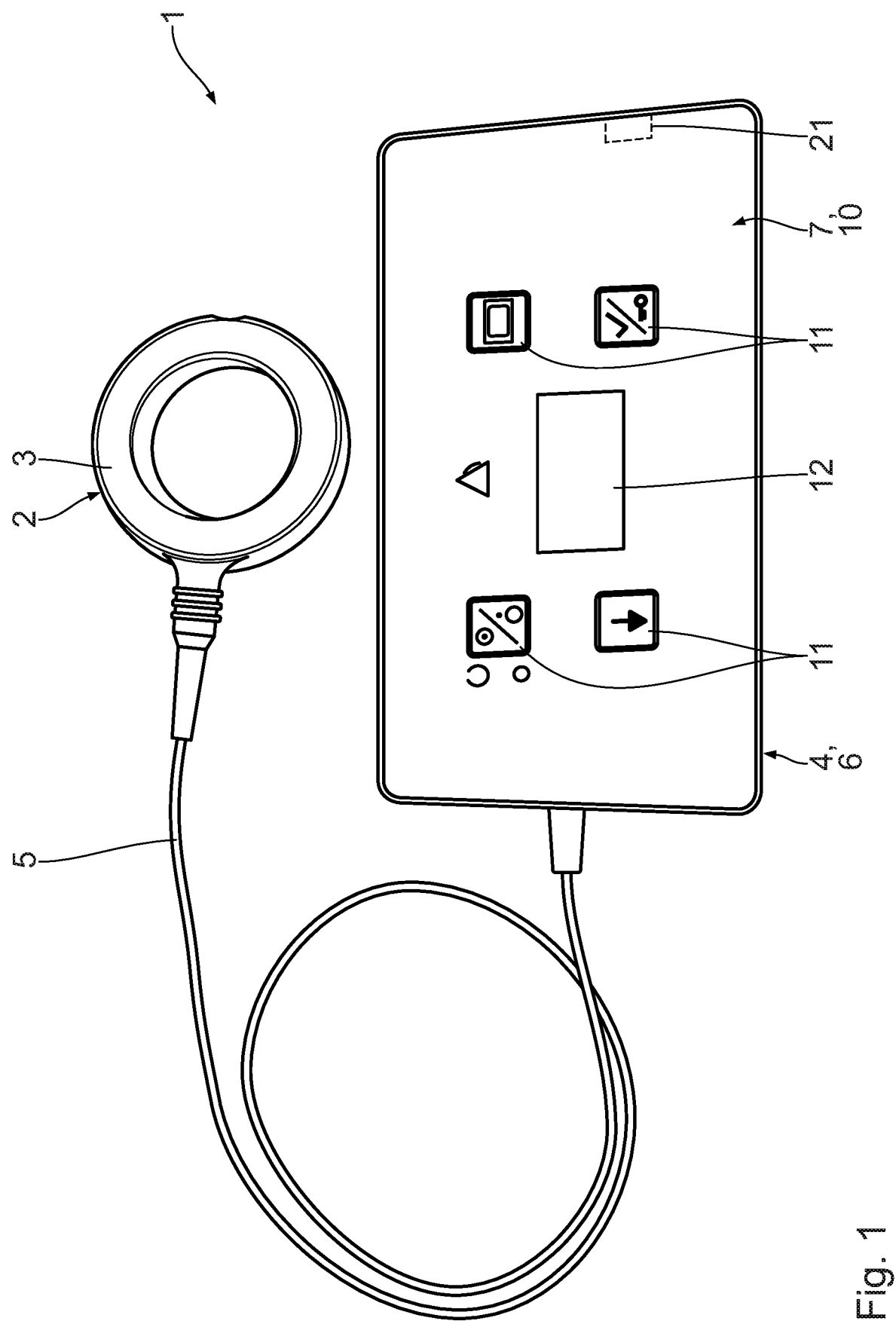
FIG. 1 shows a transmission apparatus for the transmission of brain parameter sensor data as a component of a sensor system for the measurement, transmission, processing and representation of a brain parameter.

A transmission apparatus 1 presented as a whole in the figure is part of a sensor system for the measurement, transmission, processing and representation of a brain parameter. Additional components of the sensor system not shown in the figure are a brain parameter sensor as well as an external evaluation system. The transmission apparatus 1 is designed for telemetric brain parameter measurement and in particular for intra-cranial pressure measurement in a domestic patient environment.

The transmission apparatus 1 includes a receiving unit 2 with an antenna 3 that is wirelessly connected to a transmitting unit of the brain parameter sensor not shown in the figure. An implantable intracranial pressure sensor can be used as a brain pressure sensor, as is known for example from WO 2009/043 431 A1 and from WO 2013/017 440 A1.

The antenna 3 is a loop antenna configured as a coil and which can be wired as an oscillating circuit.

In addition, the transmission apparatus 1 has a data processing device 4, which is in signaling connection to the receiving unit 2 via an antenna cable 5. The antenna cable 5 has a length between 1 m and 1.5 m. The data processing device 4 has a housing 6 which has approximately the dimensions of a typical smart phone. The data processing device 4 can be carried in a belt pouch on the body of the patient.

Figure 2:
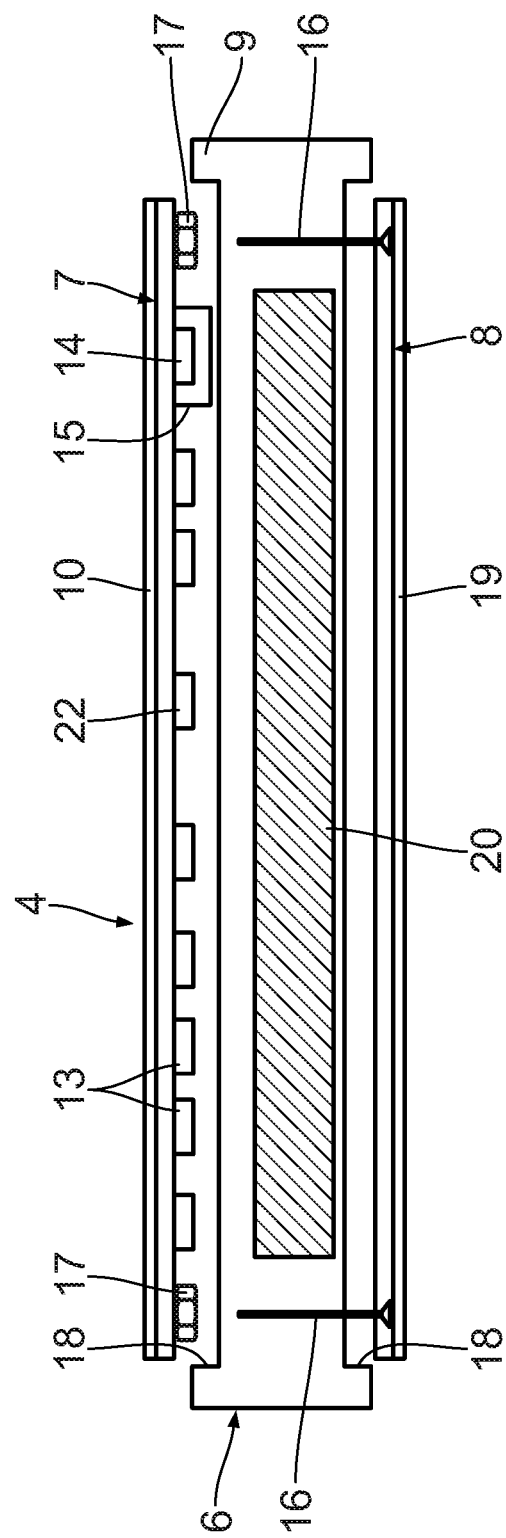
FIG. 2 shows a schematic section through a data processing device of the transmission apparatus, having a high frequency source which is integrated in a housing of the data processing device.

FIG. 2 shows details about the structure of the data processing device 4. The housing 6 of the data processing device 4 includes a metallic front plate 7, a metallic base plate 8 and a circumferential housing frame 9 made of plastic, for example made of polyoxymethylene (POM).

The front plate 7 simultaneously constitutes a printed circuit board, upon whose rear side all the electronic components of the data processing device 4 are arranged. A front side of the front plate 7 bears a membrane keyboard 10 with a total of four control keys 11 and a central display 12 (cf. FIG. 1).

On the rear, the front plate/printed circuit board 7 bears the electronic components, in particular in the form of an SMD assembly with integrated logic and memory chips 13. On the rear, the printed circuit board 7 also bears a high frequency source 14. The latter serves the purpose of generation of a data transmission carrier frequency for the transmission of sensor raw data from the brain parameter sensor via the receiving unit 2 to the data processing device 4.

The high frequency source 14 is integrated in the housing 6 of the data processing device 4.

The data processing device 4 can have the function of an RFID reader.

A metallic shielding unit 15 is used to shield the high frequency source 14 from the electronic components 13 of the data processing device 4. The shielding unit is configured as a sheet metal housing surrounding the high frequency source 14.

The front plate 7 and the base plate 8 are screwed to one another with the help of screws 16 which are inserted through holes in the base plate 8, and with the help of threaded nuts 17 firmly connected to the front plate 7, wherein the plates 7, 8 engage in recesses 18 in the housing frame 9 so that the front plate 7 on the one hand and the base plate 8 on the other hand are inserted flush in the circumferential housing frame 9 in the mounted state.

The base plate 8 also bears a film 19 on the visible side. The film 19 can have an identification plate of the data processing device 4 or of the entire sensor system 1. The film 19 can in addition be for decorative purposes and for example cover up fastening elements with which the base plate 8 and the housing frame 9 as well as the front plate 7 are connected to one another.

In addition, a battery 20 is placed in the housing 6 for supplying power to the transmission apparatus 1. The battery 20 can be charged via a power supply unit (not shown in the figure) that can be connected to the data processing device 4.

The data processing device 4 has in addition another interface 21, which is schematically indicated in dashed lines in FIG. 1 and which can be configured as a USB port. Here a transmission of brain parameter data can take place via a USB stick from a memory 22 of the data processing device 4 to an external device. Alternatively, or in addition, the interface 21 can be configured for wireless signal transmission, for example as a WLAN interface.

The brain parameter data can be transmitted over the interface 21 to the external evaluation system. This external evaluation system can be stationed at a clinic location.

With the help of the electronic components 13 of the data processing device 4 a calculation of measured brain parameter values can take place.

Between the brain parameter sensor and the receiving unit 2 an encrypted transmission of the brain parameter raw data measured by the sensor can take place. In the data processing device 4 a decoding of these encrypted data takes place with the assistance of the electronic components 13, in particular in a common data format, e.g. a .csv format.

A brain parameter data record processed in such a way includes a header, in which there is additional information along with the actual brain parameter data, in particular identification data for the identification of the patent, start and stop times of the brain parameter measurement as well as if applicable further data that the patient himself/herself can enter via the membrane keyboard 10.

The overall transmission apparatus 1 is configured to be weatherproof and in particular waterproof. The battery 20 is designed such that without the use of a power supply unit a mobile operation of the transmission apparatus 1 is possible for more than one day. The memory 22 is also correspondingly dimensioned, said memory whose capacity is sufficient for backing up a data quantity which can even be gathered during a period of several months.

We claim:

1. A transmission apparatus for a transmission of brain parameter sensor data, comprising:
    a receiving unit with an antenna, which is configured to be wirelessly connected to a transmitting unit of a brain parameter sensor for data transmission;
    a data processing device which is in signaling connection to the receiving unit;
    a high frequency source for generating a data transmission carrier frequency;
    wherein the high frequency source is integrated in a housing of the data processing device; and
    wherein the housing has a metallic front plate and a metallic base plate, wherein the metallic front plate and the metallic base plate are borne by a circumferential housing frame made of plastic.

2. The transmission apparatus according to claim 1, wherein electronic components of the data processing device are arranged on a single printed circuit board in the housing, wherein the high frequency source is also arranged on the printed circuit board.

3. The transmission apparatus according to claim 2, further comprising a metallic shielding unit for shielding the high frequency source from the electronic components of the data processing device.

4. The transmission apparatus according to claim 1, further comprising an interface configured for transmitting the brain parameter sensor data to an external device.

5. The sensor system and transmission apparatus according to claim 1, further comprising a circuit board received in the housing of the data processing device, the circuit board carrying a plurality of electronic components and the high frequency source.

6. The sensor system and transmission apparatus according to claim 5, further comprising electronic shielding configured for shielding the high frequency source from the plurality of electronic components of the data processing device.

7. The sensor system and transmission apparatus according to claim 6, wherein the frame made of plastic encompasses the high frequency source, the plurality of electronic components of the data processing device, and the circuit board of the data processing device, and
    wherein the metallic front plate and the metallic base plate are spaced apart by the plastic frame.

8. A sensor system with a transmission apparatus for a transmission of brain parameter sensor data comprising:
    a receiving unit that includes an antenna, the antenna adapted for being wirelessly connected to a transmitting unit of a brain parameter sensor for data transmission;
    a data processing device in communication with the receiving unit; the data processing device comprising a housing;

a high frequency source for generating a data transmission carrier frequency;

a circuit board received in the housing of the data processing device, the circuit board carrying a plurality of electronic components and the high frequency source; and electronic shielding configured for shielding the high frequency source from the plurality of electronic components of the data processing device;

wherein the housing is formed of (a) a plastic frame encompassing the high frequency source, the plurality of electronic components of the data processing device, and the circuit board of the data processing device, and (b) a pair of metallic plates spaced apart by the plastic frame; and wherein the high frequency source is carried by the housing of the data processing device.

9. The sensor system and transmission apparatus according to claim 8, wherein the plurality of electronic components comprise a surface mount device (SMD) assembly with integrated logic and memory and onboard memory.

10. The sensor system and transmission apparatus according to claim 8, wherein the receiving unit is connected to the data processing unit by a cable.

11. The sensor system and transmission apparatus according to claim 8, further comprising an interface configured for transmitting the brain parameter sensor data to an external device.

12. A transmission apparatus for a transmission of brain parameter sensor data, comprising:

a receiving unit with an antenna, which is configured to be wirelessly connected to a transmitting unit of a brain parameter sensor for data transmission;

a data processing device which is in signaling connection to the receiving unit;

a high frequency source for generating a data transmission carrier frequency;

a circuit board received in the housing of the data processing device, the circuit board carrying a plurality of electronic components and the high frequency source; and electronic shielding configured for shielding the high frequency source from the plurality of electronic components of the data processing device;

wherein the housing is formed of (a) a plastic frame encompassing the high frequency source, the plurality of electronic components, and the circuit board of the data processing device, and (b) a pair of metallic plates spaced apart by the plastic frame; and wherein the high frequency source is integrated in a housing of the data processing device.

13. The sensor system and transmission apparatus according to claim 12, wherein the plurality of electronic components comprise a service mount device (SMD) assembly with integrated logic and memory and onboard memory.

14. The sensor system and transmission apparatus according to claim 12, wherein the receiving unit is connected to the data processing unit by a cable.

15. The sensor system and transmission apparatus according to claim 12, further comprising an interface configured for transmitting the brain parameter sensor data to an external device.

* * * * *